(12) United States Patent
Ark et al.

(10) Patent No.: US 10,813,670 B2
(45) Date of Patent: Oct. 27, 2020

(54) SPINAL STABILIZATION SYSTEM

(71) Applicant: K2M, Inc., Leesburg, VA (US)

(72) Inventors: Timmon Ark, Falls Church, VA (US);
Robert Meyer, Leesburg, VA (US);
Michael Barrus, Ashburn, VA (US)

(73) Assignee: K2M, Inc., Leesburg, VA (US)

( * ) Notice: Subject to any disclaimer, the term of this patent is extended or adjusted under 35 U.S.C. 154(b) by 8 days.

(21) Appl. No.: 15/795,929

(22) Filed: Oct. 27, 2017

(65) Prior Publication Data
US 2018/0049776 A1 Feb. 22, 2018

Related U.S. Application Data

(62) Division of application No. 13/675,189, filed on Nov. 13, 2012, now Pat. No. 9,827,018.

(51) Int. Cl.
*A61B 17/70* (2006.01)
*A61B 17/88* (2006.01)
*A61B 90/00* (2016.01)

(52) U.S. Cl.
CPC ........ *A61B 17/7032* (2013.01); *A61B 17/701* (2013.01); *A61B 17/7034* (2013.01); *A61B 17/8863* (2013.01); *A61B 2090/037* (2016.02)

(58) Field of Classification Search
CPC .......................................... A61B 17/70–7046
See application file for complete search history.

(56) References Cited

U.S. PATENT DOCUMENTS

| | | | |
|---|---|---|---|
| 5,217,497 A | 6/1993 | Mehdian |
| 5,261,912 A | 11/1993 | Frigg |
| 5,591,235 A | 1/1997 | Kuslich |
| 5,658,286 A | 8/1997 | Sava |
| 5,667,508 A | 9/1997 | Errico et al. |
| 5,899,904 A | 5/1999 | Errico et al. |
| 5,910,142 A | 6/1999 | Tatar |
| 5,947,969 A | 9/1999 | Errico et al. |
| 5,989,250 A | 11/1999 | Wagner et al. |
| 6,102,912 A | 8/2000 | Cazin et al. |
| 6,451,021 B1 | 9/2002 | Ralph et al. |
| 6,482,207 B1 | 11/2002 | Errico |
| 6,540,749 B2 | 4/2003 | Schafer et al. |
| 6,582,434 B2 | 6/2003 | Kawakami et al. |
| 6,595,992 B1 | 7/2003 | Wagner et al. |

(Continued)

*Primary Examiner* — Nicholas J Plionis
*Assistant Examiner* — Steven J Cotroneo
(74) *Attorney, Agent, or Firm* — Lerner, David, Littenberg, Krumholz & Mentlik, LLP

(57) ABSTRACT

A spinal stabilization system including a connecting rod and a bone screw. The connecting rod includes an elongate rounded section, an elongate head portion, and a neck portion connecting the elongate rounded section with the elongate head portion. The bone screw includes a head portion defining a slot, a shank extending longitudinally from the head portion, and a set screw configured to secure the connecting rod in the slot. The head portion includes a pair of radially opposing walls defining the slot therebetween. The head portion includes a trailing end and a leading end. The trailing end includes a guide member defining an aperture configured and dimensioned to receive the set screw therethrough. The aperture is in communication with the slot. In particular, the guide member interconnects the pair of radially opposing walls.

17 Claims, 9 Drawing Sheets

(56) References Cited

U.S. PATENT DOCUMENTS

| | | | |
|---|---|---|---|
| 6,644,087 B1 | 11/2003 | Ralph et al. | |
| 7,503,918 B2 | 3/2009 | Baccelli et al. | |
| 7,507,248 B2 * | 3/2009 | Beaurain | A61B 17/7037 606/261 |
| 7,520,879 B2 | 4/2009 | Justis et al. | |
| 7,563,274 B2 * | 7/2009 | Justis | A61B 17/701 606/246 |
| 7,569,061 B2 | 8/2009 | Colleran | |
| 7,588,575 B2 | 9/2009 | Colleran et al. | |
| 7,588,588 B2 | 9/2009 | Spitler et al. | |
| 7,604,653 B2 | 10/2009 | Kitchen | |
| 7,618,442 B2 | 11/2009 | Spitler et al. | |
| 7,674,277 B2 * | 3/2010 | Burd | A61B 17/7032 606/265 |
| 7,766,942 B2 * | 8/2010 | Patterson | A61B 17/7011 606/254 |
| 7,931,676 B2 | 4/2011 | Veldman et al. | |
| 9,295,494 B2 | 3/2016 | Strauss et al. | |
| 9,827,018 B2 | 11/2017 | Ark et al. | |
| 2002/0161368 A1 | 10/2002 | Foley et al. | |
| 2005/0065515 A1 | 3/2005 | Jahng | |
| 2005/0107788 A1 * | 5/2005 | Beaurain | A61B 17/6483 606/308 |
| 2005/0273099 A1 | 12/2005 | Baccelli et al. | |
| 2008/0086130 A1 * | 4/2008 | Lake | A61B 17/701 606/86 R |
| 2008/0262546 A1 * | 10/2008 | Calvosa | A61B 17/701 606/250 |
| 2009/0048632 A1 * | 2/2009 | Firkins | A61B 17/701 606/246 |
| 2009/0088800 A1 * | 4/2009 | Blain | A61B 17/7005 606/246 |
| 2009/0138044 A1 * | 5/2009 | Bergeron | A61B 17/1655 606/246 |
| 2009/0198279 A1 * | 8/2009 | Zhang | A61B 17/7023 606/264 |
| 2010/0063544 A1 * | 3/2010 | Butler | A61B 17/701 606/261 |
| 2010/0137920 A1 * | 6/2010 | Hammill, Sr. | A61B 17/7034 606/308 |
| 2011/0190823 A1 | 8/2011 | Bergeron et al. | |

* cited by examiner

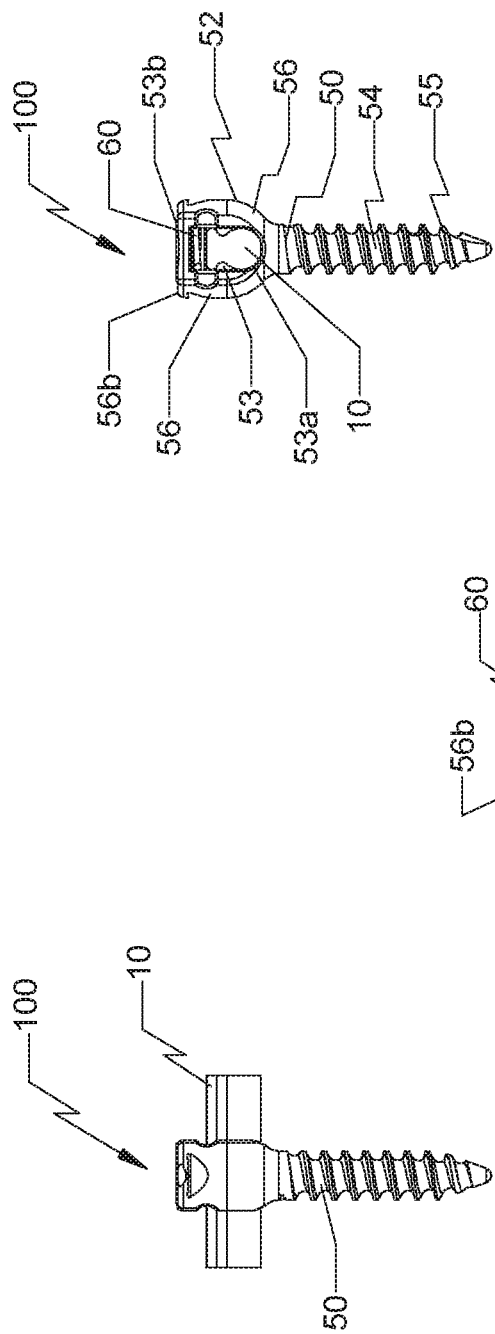

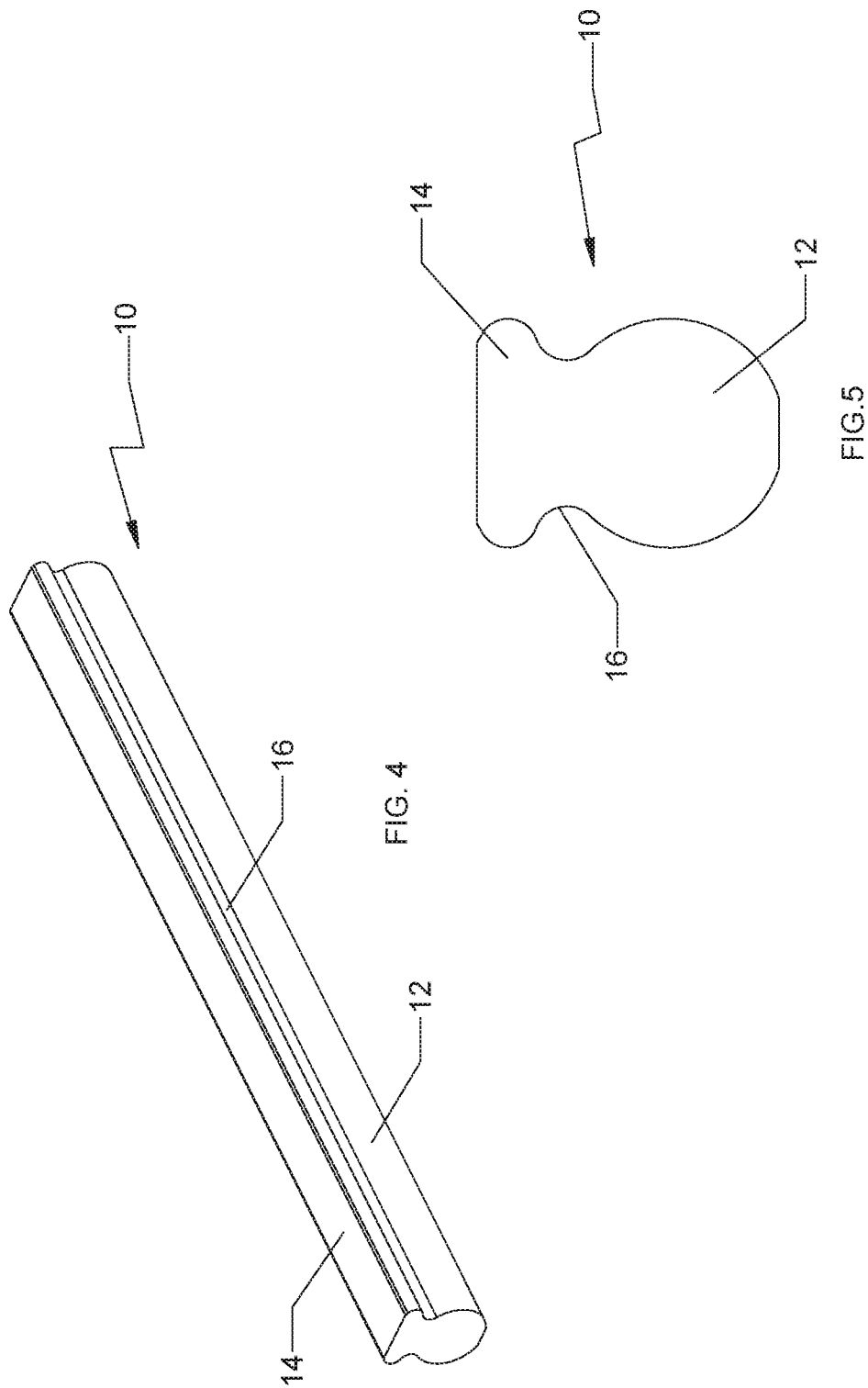

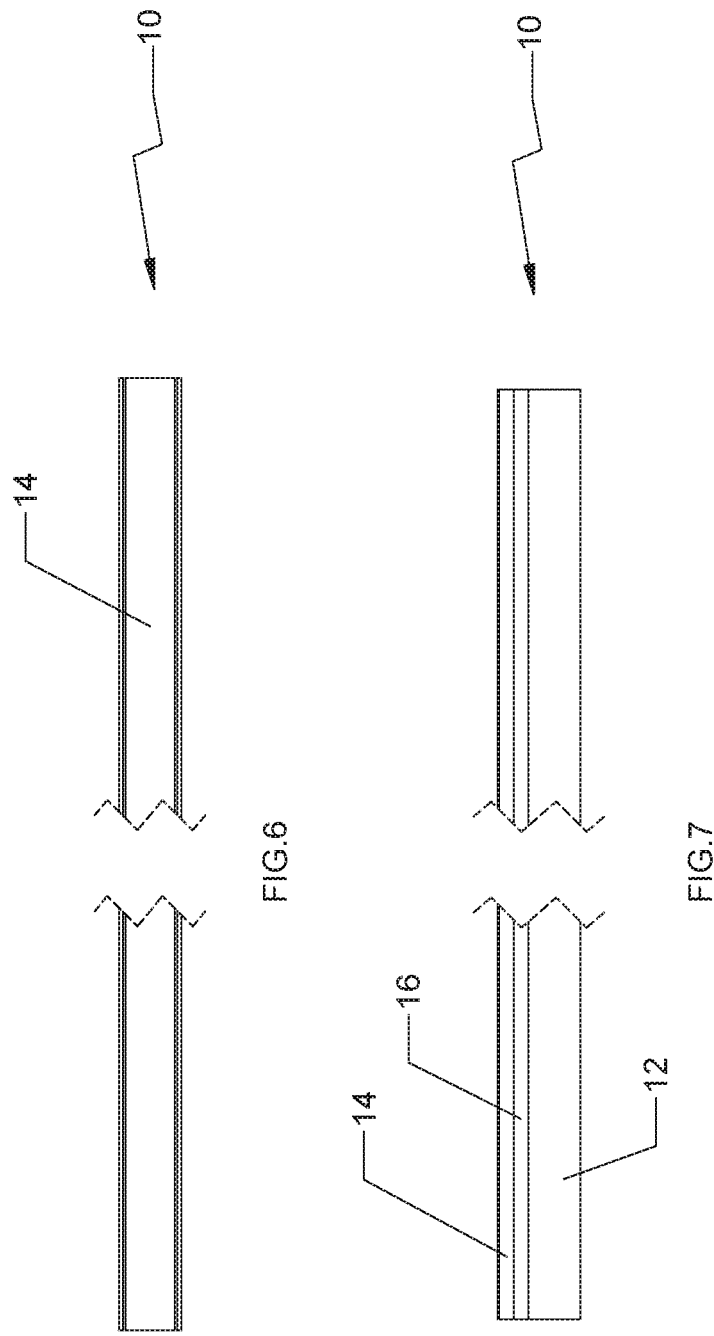

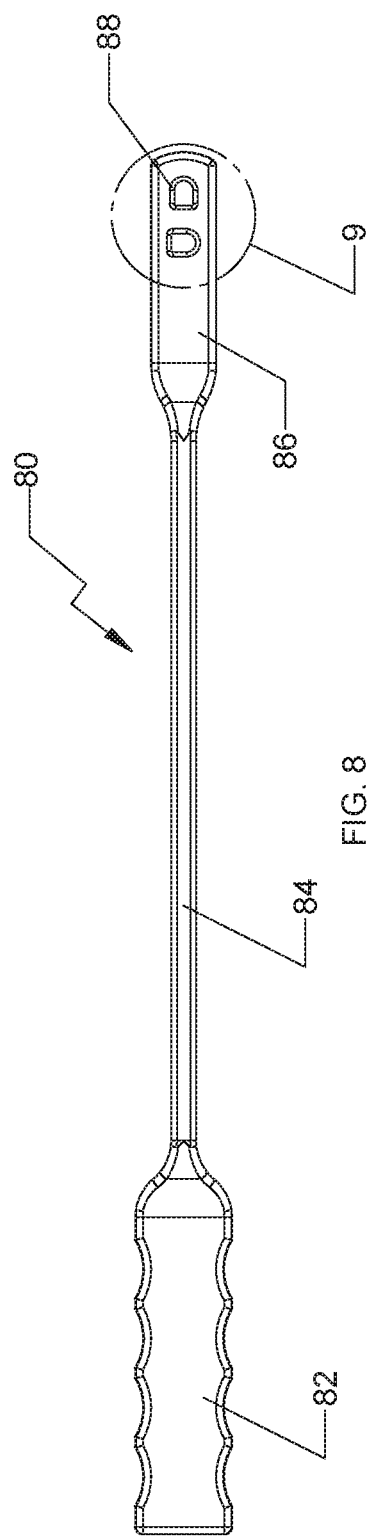
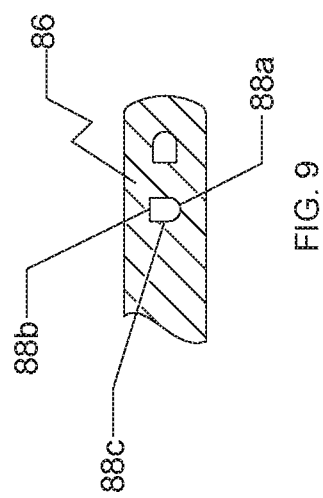

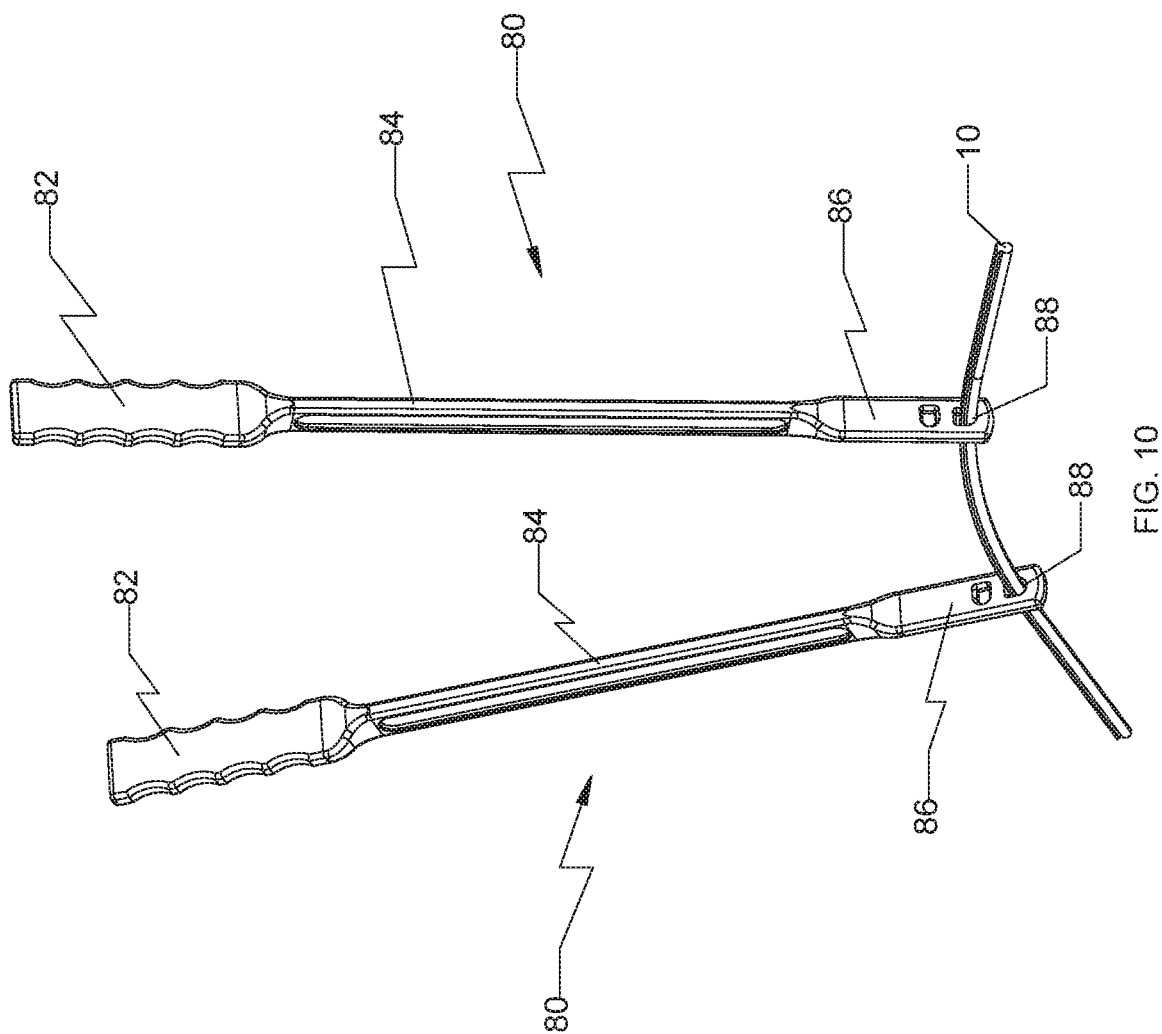

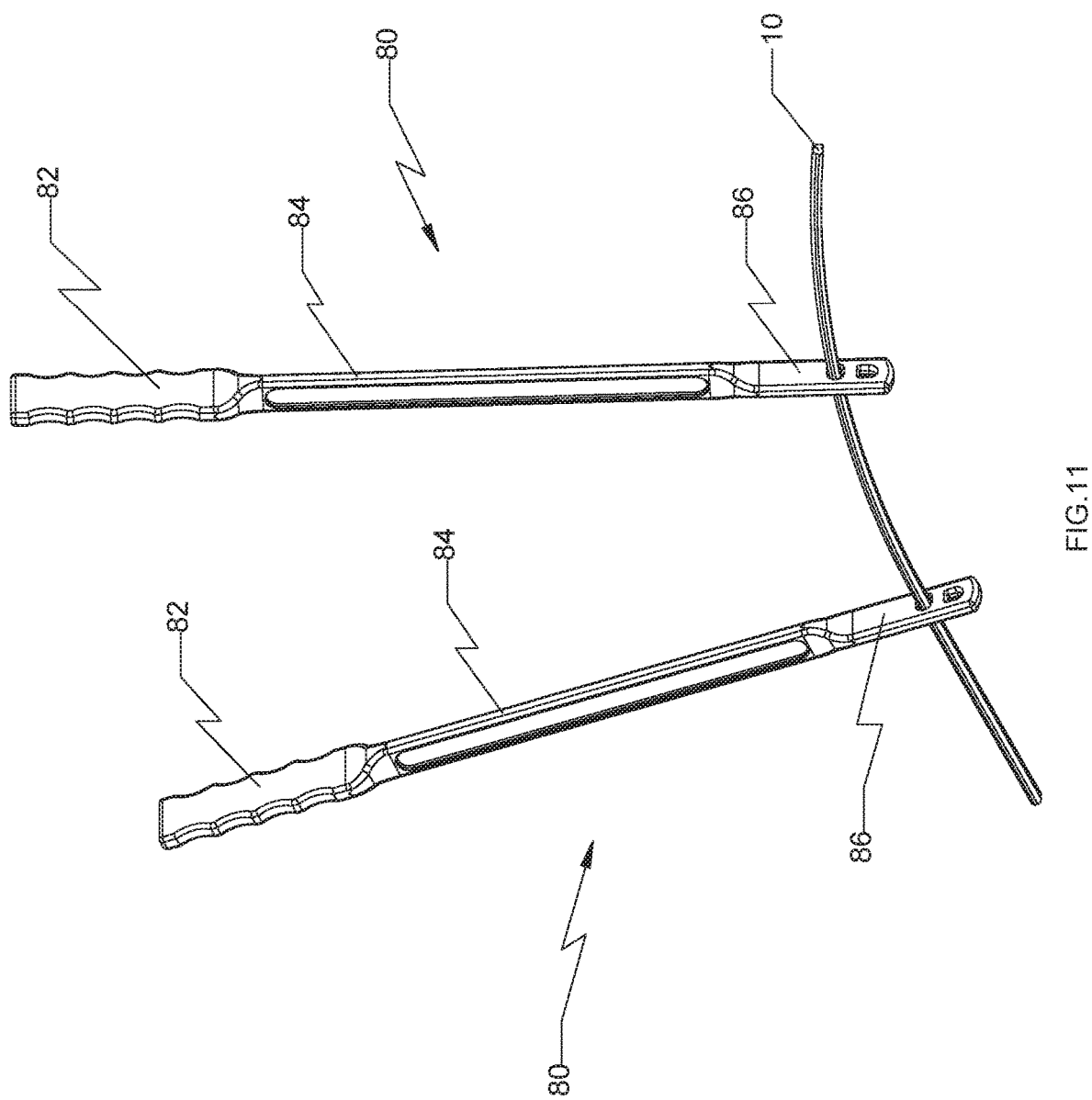

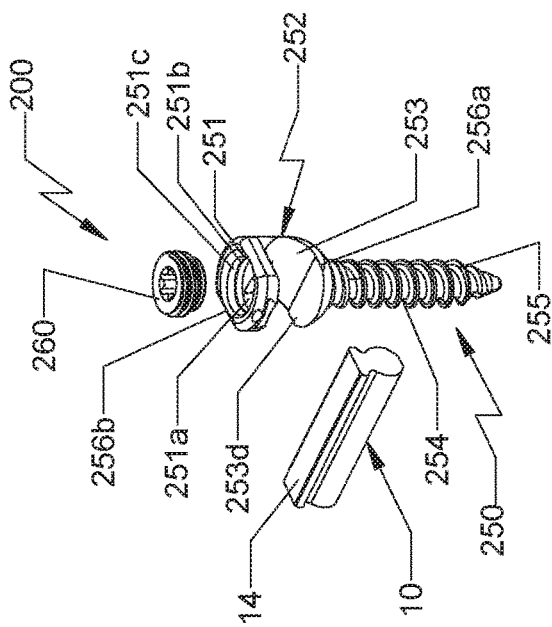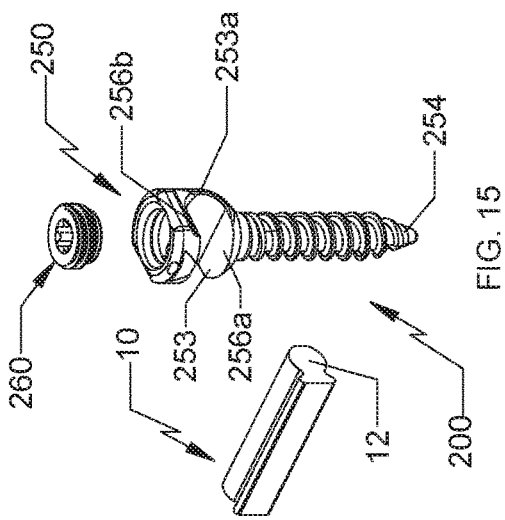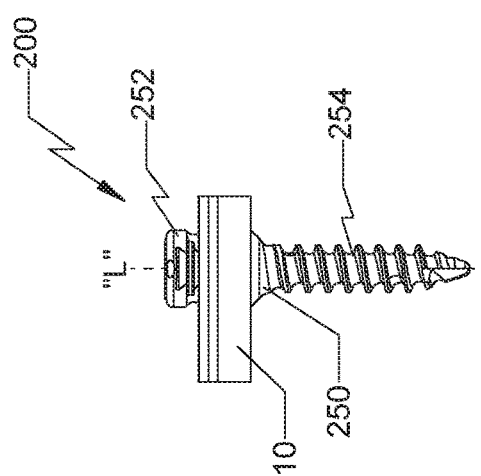

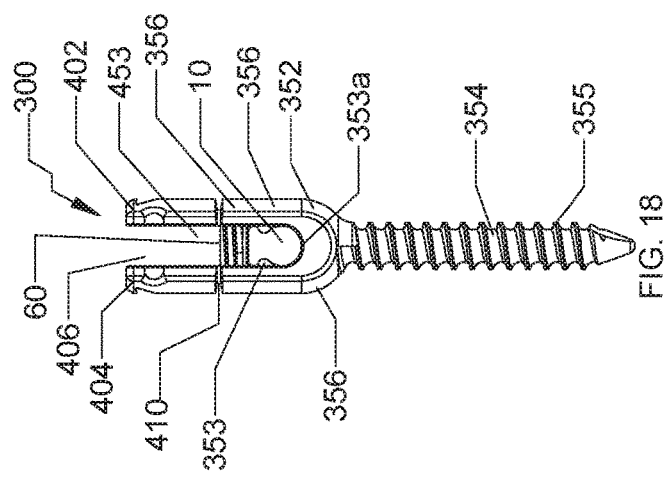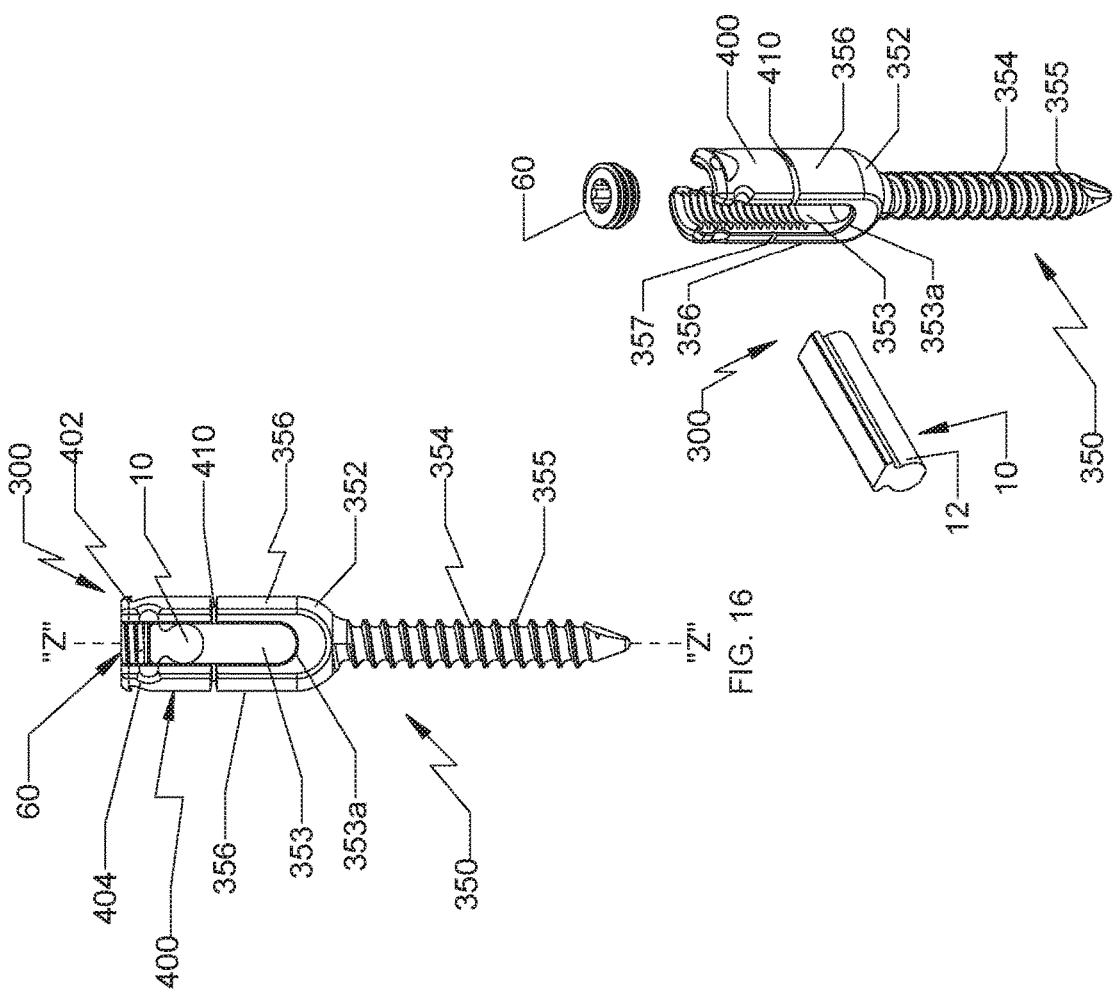

SPINAL STABILIZATION SYSTEM

CROSS-REFERENCE TO RELATED APPLICATION

This application is a divisional application of U.S. patent application Ser. No. 13/675,189, filed Nov. 13, 2012, the entire contents of which is incorporated herein by reference.

BACKGROUND

Technical Field

The present disclosure relates to orthopedic surgical devices and, more particularly, to a spinal stabilization system.

Background of Related Art

The spinal column is a complex system of bones and connective tissues that provide support for the human body and protection for the spinal cord and nerves. The adult spine is comprised of an upper and lower portion. The upper portion contains twenty-four discrete bones, which are subdivided into three areas including seven cervical vertebrae, twelve thoracic vertebrae, and five lumbar vertebrae. The lower portion is comprised of the sacral and coccygeal bones. The cylindrical shaped bones, called vertebral bodies, progressively increase in size from the upper portion downwards to the lower portion.

An intervertebral disc along with two posterior facet joints cushion and dampen the various translational and rotational forces exerted upon the spinal column. The intervertebral disc is a spacer located between two vertebral bodies. The facets provide stability to the posterior portion of adjacent vertebrae. The spinal cord is housed in the canal of the vertebral bodies. It is protected posteriorly by the lamina. The lamina is a curved surface with three main protrusions. Two transverse processes extend laterally from the lamina, while the spinous process extends caudally and posteriorly. The vertebral bodies and lamina are connected by a bone bridge called the pedicle.

The spine is a flexible structure capable of a large range of motion. There are various disorders, diseases and types of injury, which restrict the range of motion of the spine or interfere with important elements of the nervous system. The problems include, but are not limited to, scoliosis, kyphosis, excessive lordosis, spondylolisthesis, slipped or ruptured discs, degenerative disc disease, vertebral body fracture, and tumors. Persons suffering from any of the above conditions typically experience extreme or debilitating pain and often times diminished nerve function. These conditions and their treatments can be further complicated if the patient is suffering from osteoporosis, or bone tissue thinning and loss of bone density.

Spinal fixation apparatuses are widely employed in surgical processes for correcting spinal injuries and diseases. When the disc has degenerated to the point of requiring removal, there are a variety of interbody implants that are utilized to take the place of the disc. These include interbody spacers, metal cages and cadaver and human bone implants. In order to facilitate stabilizing the spine and keeping the interbody in position, other implants are commonly employed, such as bone screws and connecting rods.

Often times, the surgeon needs to make adjustments to the orientation and/or position of the connecting rod relative to the bone screw. Therefore, a need exists for a simple and effective screw and rod construct that enables surgeons to easily and safely manipulate the connecting rod relative to the bone screws during a surgical procedure.

SUMMARY

In accordance with an embodiment of the present disclosure, there is provided a spinal stabilization system including a connecting rod and a bone screw. The connecting rod includes an elongate rounded section, an elongate head portion, and a neck portion connecting the elongate rounded section with the elongate head portion. The bone screw includes a head portion defining a slot, a shank extending longitudinally from the head portion, and a set screw configured to secure the connecting rod in the slot. The head portion includes a pair of radially opposing walls defining the slot therebetween. The head portion includes a trailing end and a leading end. The trailing end includes a guide member defining an aperture configured and dimensioned to receive the set screw therethrough. The aperture is in communication with the slot. The guide member interconnects the pair of radially opposing walls.

In an embodiment, the guide member may include a lip extending radially inward. The slot may include a leading end portion configured to receive the elongate rounded section of the connecting rod and a trailing end portion configured to threadably engage the set screw. The leading end portion of the slot may have an arcuate configuration dimensioned to accommodate a circular cross-section of the elongate rounded section of the connecting rod. In another embodiment, the slot may have a U-shaped profile. Moreover, the pair of walls of the head portion of the bone screw may include internal threads.

In accordance with another embodiment of the present disclosure, there is provided a spinal stabilization system including a connecting rod and a bone screw. The connecting rod includes an elongate rounded section, an elongate head portion, and a neck portion connecting the elongate rounded section with the elongate head portion. The bone screw includes a head portion defining a slot, a shank extending longitudinally from the head portion, and a set screw configured to secure the connecting rod in the slot. The head portion includes a leading wall, a trailing wall, and a transverse wall connecting the leading and trailing walls. In particular, the leading and trailing walls define the slot therebetween. The trailing wall defines an aperture configured and dimensioned to receive the set screw therethrough. The aperture is in communication with the slot. The transverse wall includes an arcuate portion configured to receive the elongate rounded section of the connecting rod.

In an embodiment, the trailing wall may include a lip extending radially inward, the lip defining the aperture. The lip may include threads configured to engage threads on the set screw. In another embodiment, the slot may be substantially U-shaped. In particular, the slot may be substantially orthogonal to a longitudinal axis defined by the bone screw.

In accordance with yet another embodiment of the present disclosure, there is provided a spinal stabilization system including a connecting rod, a bone screw, and a loading unit. The connecting rod includes an elongate rounded section, an elongate head portion, and a neck portion connecting the elongate rounded section with the elongate head portion. The bone screw includes a head portion defining a slot, a shank extending longitudinally from the head portion, and a set screw configured to secure the connecting rod in the slot. The head portion includes a pair of radially opposing walls defining the slot therebetween. The loading unit is detachably coupled with the head portion of the bone screw. The loading unit includes a pair of opposing arms defining a gap therebetween, wherein the gap is configured and dimensioned to retain the connecting rod and the set screw in place.

In an embodiment, inner walls of the pair of opposing arms may include threads. In addition, the pair of opposing arms may have a weakened region. Moreover, the pair of opposing arms may include a friction fit configuration to retain the connecting rod in the gap.

In another embodiment, the slot may have a U-shaped configuration. The slot of the bone screw and the gap defined between the pair of opposing arms of the loading unit may be longitudinally aligned. A leading end portion of the slot may have an arcuate configuration dimensioned to accommodate a circular cross-section of the elongate rounded section of the connecting rod.

BRIEF DESCRIPTION OF THE DRAWINGS

The foregoing and other features of the present disclosure will become apparent to one skilled in the art to which the present disclosure relates upon consideration of the following description of the disclosure with reference to the accompanying drawings, wherein:

FIG. 1 is a side view of a spinal stabilization system in accordance with an embodiment of the present disclosure;

FIG. 2 is an end view of the spinal stabilization system of FIG. 1;

FIG. 3 is an exploded perspective view of the spinal stabilization system of FIG. 1 with parts separated;

FIG. 4 is a perspective view of a connecting rod of the spinal stabilization system of FIG. 1;

FIG. 5 is an end view of the connecting rod of FIG. 4;

FIG. 6 is a top view of the connecting rod of FIG. 4;

FIG. 7 is a side view of the connecting rod of FIG. 4;

FIG. 8 is a side view of a rod bender device for use with the spinal stabilization system of FIG. 1;

FIG. 9 is a side cross-sectional view of the area of detail indicated in FIG. 8;

FIG. 10 is a perspective view of a pair of rod bender devices of FIG. 8 having the connecting rod of FIG. 4 inserted therethrough;

FIG. 11 is a perspective view of the pair of rod bender devices of FIG. 8 having the connecting rod of FIG. 4 inserted therethrough in a different orientation;

FIG. 12 is a side view of a spinal stabilization system in accordance with another embodiment of the present disclosure;

FIG. 13 is an exploded perspective view of the spinal stabilization system of FIG. 12 with parts separated;

FIG. 14 is a side view of the spinal stabilization system of FIG. 12 illustrating a placement of a connecting rod in a different orientation;

FIG. 15 is an exploded perspective view of the spinal stabilization system of FIG. 14;

FIG. 16 is an end view of a spinal stabilization system in accordance with yet another embodiment of the present disclosure;

FIG. 17 is an exploded perspective view of the spinal stabilization system of FIG. 16;

FIG. 18 is an end view of the spinal stabilization system of FIG. 16 after a reduction of a connecting rod;

DETAILED DESCRIPTION OF EMBODIMENTS

Figure 20:
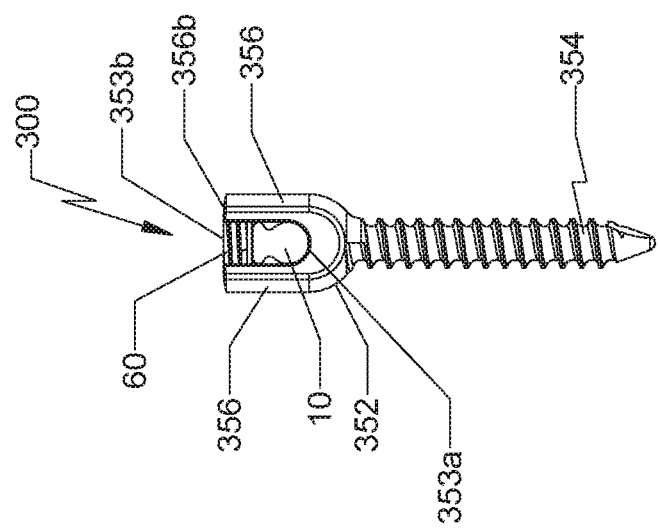
FIG. 20 is an end view of the spinal stabilization system of FIG. 19.

Embodiments of the present disclosure will now be described in detail with reference to the drawings, in which like reference numerals designate identical or corresponding elements in each of the several views. As used herein, the term "distal," as is conventional, will refer to that portion of the instrument, apparatus, device or component thereof which is farther from the user while, the term "proximal," will refer to that portion of the instrument, apparatus, device or component thereof which is closer to the user. In addition, the term "cephalad" is used in this application to indicate a direction toward a patient's head, while the term "caudad" indicates a direction toward the patient's feet. Further still, for the purposes of this application, the term "medial" indicates a direction toward the middle of the body of the patient, while the term "lateral" indicates a direction toward a side of the body of the patient, i.e., away from the middle of the body of the patient. The term "posterior" indicates a direction toward the patient's back, while the term "anterior" indicates a direction toward the patient's front. In the following description, well-known functions or constructions are not described in detail to avoid obscuring the present disclosure in unnecessary detail.

With reference to FIGS. 1-3, an embodiment of the present disclosure is shown generally as a spinal stabilization system 100. Spinal stabilization system 100 includes at least one bone screw 50 and a connecting rod 10. Connecting rod 10 is configured and dimensioned to be selectively and releasably secured to bone screw 50. Connecting rod 10 is defined by an elongate body of a particular length. The elongate body is made of a biocompatible material such as Titanium (Ti-CP) and its alloys (e.g., Ti-6A1-4V), Cobalt-Chrome Alloy (CoCr), or Stainless Steel (SS).

With reference to FIGS. 4 and 5, the elongate body of connecting rod 10 includes an elongate rounded section 12 having a substantially circular cross-section, an elongate head portion 14, and a neck portion 16 that connects and transitions elongate rounded section 12 into elongate head portion 14, thereby providing reduced stress concentration along the elongate body of connecting rod 10. Neck portion 16 may define a pair of concave sides joining elongate head portion 14 to elongate rounded section 12. The elongate body of connecting rod 10 may be monolithically formed as a unitary construct. For example, connecting rod 10 may be machined from a single piece of bar stock.

With particular reference to FIG. 5, elongate head portion 14 has a non-circular cross-section. As shown, elongate head portion 14 has a substantially rectangular cross-section having suitable dimensions of, for example, about 6 mm×about 1 mm (0.246 in.×0.039 in.). However, it is envisioned that elongate head portion 14 may have a cross-section that is substantially square, elliptical or any other shape to add rigidity to rounded section 12 of connecting rod 10.

With reference back to FIGS. 2 and 3, elongate rounded section 12 of connecting rod 10 is configured and dimensioned to be received in a slot 53 defined in a head portion 52 of bone screw 50, as will be described in detail hereinbelow. While elongate head portion 14 of connector rod 10 is disposed above elongate rounded section 12, elongate head portion 14 does not appreciably increase the height profile of the screw-rod combination. Connecting rod 10 affords greater strength and rigidity in comparison with ordinary circular rods with comparable dimensions. As such, connecting rod 10 and bone screw 50 construct affords greater rigidity and strength without increased bulk and profile.

With continued reference to FIGS. 2 and 3, bone screw 50 includes a head portion 52 configured to receive connecting rod 10 therein, a shank 54 extending longitudinally from head portion 52, and a set screw 60 threadably coupled to head portion 52 to secure connecting rod 10 in a slot 53 defined in head portion 52. Head portion 52 of bone screw 50 includes a pair of radially opposing walls 56 defining slot 53 therebetween. Radially opposing walls 56 include internal threads 57 configured for engaging external threads of set screw 60. Slot 53 defines a substantially U-shape channel configured and dimensioned to receive connecting rod 10. Slot 53 includes a leading end portion 53a and a trailing end portion 53b (FIG. 2). In particular, leading end portion 53a has an arcuate configuration configured to accommodate a circular cross-section of rounded section 12 of connecting rod 10. Trailing end portion 53b of slot 53 includes a pair of opposing guide members 51 (FIG. 3) defining an aperture 51a configured and dimensioned to receive set screw 60 therethrough. Moreover, the pair of opposing guide members 51 includes a lip 51b extending radially inward and defining an acute angle with respect to trailing end portion 53b of slot 53 to facilitate centering and/or insertion of set screw 60 within aperture 51a. Moreover, the pair of opposing guide members 51 inhibits flexing of the pair of radially opposing walls 56 defining slot 53 therebetween. In this manner, connecting rod 10 is securely positioned in slot 53 defined between the pair of radially opposing walls 56. Under such a configuration, connecting rod 10 is inserted into slot 53 through a lateral opening 53c defined in a lateral side of head portion 52 of bone screw 50. Additionally, trailing end portion 53b of slot 53 defines a substantially planar surface such that set screw 60 threadably inserted in slot 53 is substantially flush with trailing end portions 56b of the respective walls 56 when connecting rod 10 is positioned within slot 53 and secured by set screw 60 therein.

With continued reference to FIGS. 2 and 3, shank 54 includes threads 55 for engagement through vertebral bodies. Bone screw 50 may be made of a biocompatible material such as Titanium (Ti-CP) and its alloys (e.g., Ti-6A1-4V), Cobalt-Chrome Alloy (CoCr) or Stainless Steel (SS). In particular, head portion 52 and shank 54 may be monolithically formed.

With reference now to FIGS. 8-11, spinal stabilization system 100 may further include rod bender devices 80. Each rod bender devices 80 define matching apertures 88 configured to receive and hold at least a portion of connecting rod 10 therein. Rod bender device 80 includes a handle member 82, an elongate body 84 extending distally from handle portion 82, and an engaging portion 86 coupled to elongate body 84. Elongate body 84 is coupled or formed with handle member 82 and engaging portion 86 so as to reduce stress concentration. Handle member 82 may contain scalloped sections to facilitate gripping by the user. Elongate body 84 may have a rectangular cross-section and may define a cavity along the length thereof to reduce the weight of device. Engaging portion 86 defines at least one aperture 88 adapted and dimensioned to receive therethrough connecting rod 10. In particular, inner walls that define aperture 88 are configured to permit insertion of connecting rod 10 through aperture 88 in a single orientation with respect to such aperture.

Each aperture 88 includes an arcuate end wall 88a configured to engage elongate rounded section 12 of connecting rod 10, an opposite substantially straight end wall 88b configured to engage the substantially flat portion of elongate head portion 14 of connecting rod 10, and connecting side walls 88c connecting arcuate end wall 88a and the substantially straight end wall 88b. In this manner, connecting rod 10 is inserted into each aperture 88 in a single orientation. Thus, in order to accommodate insertion of connecting rod in aperture 88 in various orientations, a plurality of apertures 88 are defined in engaging portion 86 in different orientations, as shown in FIGS. 10 and 11. For example, the pair of apertures 88 defined in engaging portion 86 is oriented at a 90-degree angle, whereby the rectangular portions of apertures 88 are orthogonal to each other. In this manner, the user can bend connecting rod 10 in both an anterior-posterior orientation and a medial-lateral orientation. It is also contemplated that connecting rod 10 may be inserted in non-corresponding apertures 88 in rod bender devices 80 to facilitate twisting of connecting rod 10, if necessary or desired.

The length of elongate body 84 may be tailored to meet the needs of the surgical application to provide a suitable long moment arm necessary to provide the user a mechanical advantage to bend connecting rod 10. In addition, it is also envisioned that elongate body 84 may be a hollow tubular member and/or define lightening holes to reduce the weight of device 80.

In use, the user implants a plurality of bone screws 50 in vertebral bodies of a patient. Threaded shank 54 can be driven into the desired vertebral body by providing torsional force via a driving tool (not shown) configured to mate with and grip bone screw 50. After shank 54 is positioned within the vertebral body and the driving tool is removed from bone screw 50, connecting rod 10 is positioned within slot 53 of head portion 52.

In particular, spinal stabilization system 100 can be utilized to correct spinal deformity. Prior to securing connecting rod 10 with bone screw 50, the surgeon can manipulate and correct the curve of the spinal column, i.e., to manually manipulate and reduce the "rib hump." After placing the spine in proper position, the surgeon can bend connecting rod 10 prior to securing connecting rod 10 to the first two points of the spinal column where the construct is to be attached.

The surgeon can bend connecting rod 10 by utilizing the pair of rod bender devices 80. In use, connecting rod 10 is inserted through apertures 88 of rod bender devices 80 and force is applied at handle members 82 of rod bender devices 80 to appropriately contour and shape connecting rod 10 to a desired curve.

At this time, connecting rod 10 is positioned in respective slots 53 of bone screws 50 implanted in vertebral bodies. Set screws 60 can now be threadably inserted into head portion 52 of bone screw 50. The rod and bone screw combination of the present disclosure may provide particular advantages in, e.g., scoliosis or other spinal deformity surgery, in which high stress levels are exerted upon such constructs at particular levels in the construct or over the entire length of such a construct.

With reference now to FIGS. 12 and 13, another embodiment of the present disclosure is shown generally as a spinal stabilization system 200. Spinal stabilization system 200 includes at least one bone screw 250 and a connecting rod 10. Connecting rod 10 is configured and dimensioned to be selectively and releasably secured to bone screw 250. Connecting rod 10 is defined by an elongate body of a particular length. The elongate body is made of a biocompatible material such as Titanium (Ti-CP) and its alloys (e.g., Ti-6A1-4V), Cobalt-Chrome Alloy (CoCr), or Stainless Steel (SS).

With continued reference to FIGS. 12 and 13, bone screw 250 includes a head portion 252 configured to receive connecting rod 10 therein, a shank 254 extending longitudinally from head portion 252, and a set screw 260 threadably coupled to head portion 252 to secure connecting rod 10 in a slot 253 defined in head portion 252. Head portion 252 of bone screw 250 includes a pair of opposing leading and trailing walls 256a, 256b defining slot 253 therebetween.

With particular reference to FIG. 13, trailing wall 256b defines an aperture 251a configured and dimensioned to receive a set screw 260 therethrough. Trailing wall 256b includes a lip 251 extending radially inward to facilitate centering and/or insertion of set screw 60 within aperture 251a. Moreover, an inner surface 251b of lip 251 includes threads 251c configured to engage external threads of set screw 260.

Slot 253 defines a substantially U-shaped channel configured and dimensioned to receive connecting rod 10 therein. In contrast to slot 53 of bone screw 50, the U-shaped channel is rotated 90 degrees, whereby the U-shape channel of slot 253 is substantially orthogonal to a longitudinal axis "L-L" (FIG. 12) defined by bone screw 250. Slot 253 includes an arcuate portion 253a configured and dimensioned to accommodate a circular cross-section of rounded section 12 of connecting rod 10. In addition, inner sides of leading and trailing walls 256a, 256b that define slot 253 are substantially flat to provide a planar contact with elongate head portion 14 of connecting rod 10. Under such a configuration, once connecting rod 10 is disposed within slot 253, elongate head portion 14 of connecting rod 10 engages one or both of leading and trailing walls 256a, 256b to inhibit movement and rotation within slot 253.

With particular reference to FIG. 12, slot 253 is dimensioned such that when connecting rod 10 is positioned within slot 253, as shown, elongate head portion 14 of connecting rod 10 engages inner side of trailing wall 256b. Under such a configuration, flexing of trailing wall 256b is substantially eliminated, and thereby further securing connecting rod 10 with bone screw 250. It is further contemplated that connecting rod 10 may be positioned in slot 253 such that elongate rounded section 12 of connecting rod 10 engages arcuate portion 253a of slot 253, as shown in FIGS. 14 and 15. Slot 253 is configured and dimensioned such that when connecting rod 10 is oriented in such a manner, elongate head portion 14 engages inner surfaces of leading and trailing walls 256a, 256b. Under such a configuration, rotation and movement of connecting rod 10 in slot 253 is reduced. Moreover, such a configuration further eliminates flexing of trailing wall 256 when connecting rod 10 is positioned within slot 253.

With continued reference to FIGS. 12 and 13, shank 254 includes threads 255 for engagement through vertebral bodies. Bone screw 250 may be made of a biocompatible material such as Titanium (Ti-CP) and its alloys (e.g., Ti-6A1-4V), Cobalt-Chrome Alloy (CoCr) or Stainless Steel (SS). In particular, head portion 252 and shank 254 may be monolithically formed. The method of using spinal stabilization system 200 is substantially similar to the method of using spinal stabilization system 100, described hereinabove, and thus will not be discussed herein.

With reference now to FIGS. 16 and 17, yet another embodiment of the present disclosure is shown generally as a spinal stabilization system 300. Spinal stabilization system 300 includes at least one bone screw 350, a loading unit 400, and a connecting rod 10. Connecting rod 10 is configured and dimensioned to be selectively and releasably secured to bone screw 350.

Bone screw 350 includes a head portion 352 configured to receive connecting rod 10 therein, a shank 354 extending longitudinally from head portion 352, and a set screw 60 threadably coupled to head portion 352 to secure connecting rod 10 in a slot 353 defined in head portion 352. Head portion 352 of bone screw 350 includes a pair of radially opposing walls 356 defining slot 353 therebetween. Radially opposing walls 356 include internal threads 357 configured for engaging external threads of set screw 60. Slot 353 defines a substantially U-shape channel configured and dimensioned to receive connecting rod 10. Slot 353 is aligned with a longitudinal axis "Z-Z" (FIG. 16) defined by shank 354 of bone screw 350. Slot 353 includes a leading end portion 353a and a trailing end portion 353b (FIG. 20). In particular, leading end portion 353a has an arcuate configuration configured to accommodate a circular cross-section of rounded section 12 of connecting rod 10. Trailing end portion 353b of slot 53 defines a substantially planar surface such that set screw 60 threadably inserted in slot 353 is substantially flush with trailing end portions 356b (FIG. 20) of the respective walls 356 when connecting rod 10 is positioned within slot 353 and secured by set screw 60 therein, as shown in FIG. 20.

With continued reference to FIGS. 16 and 17, a loading unit 400 is integrally formed with bone screw 350. Loading unit 400 includes a pair of opposing walls 402, 404 defining a slot 453 (FIG. 18) therebetween. Slot 453 is configured and dimensioned to receive set screw 60. Slot 453 is in communication with slot 353 of bone screw 350. Moreover, slot 453 of loading unit 400 is substantially aligned with slot 353. In particular, inner walls of the pair of opposing walls 402, 404 include threads to engage external threads on set screw 60. Loading unit 400 includes weakened regions 410 configured to facilitate detachment of loading unit 400 from head portion 352 of bone screw 350. Moreover, slot 453 is configured and dimensioned to provide a friction fit engagement with connecting rod 10. In this manner, connecting rod 10 may be retained in any position along slot 453 of loading unit 400.

Figure 19:
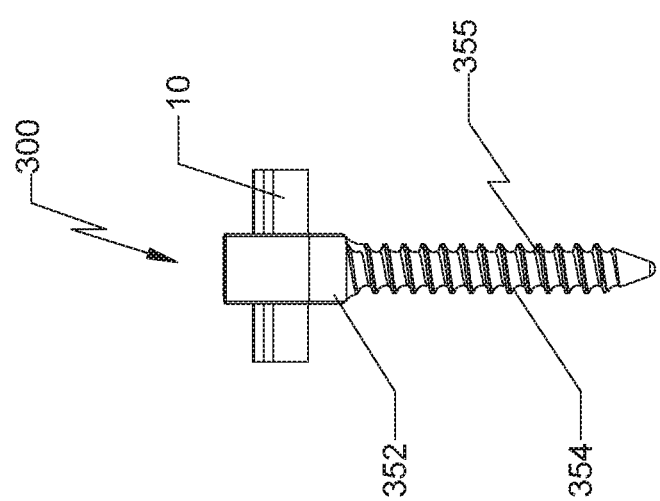
FIG. 19 is a side view of the spinal stabilization system of FIG. 16 with a loading unit detached from a bone screw.

Initially, connecting rod 10 is positioned in slot 453 of loading unit 400, as shown in FIG. 16. In this manner, the clinician does not have to place connecting rod 10 and set screw 60 with bone screw 350 in-situ. Set screw 60 threadably engages threads of inner sides of opposing walls 402, 404. To achieve reduction of connecting rod 10 in slot 353 of bone screw 350, set screw 60 and connecting rod 10 positioned in slot 453 of loading unit 400 are lowered by rotating set screw 60, which urges connecting rod 10 towards a seat of slot 353 until elongate rounded section 12 of connecting rod 10 is in contact with leading end portion 353a of slot 353. At this time, as best seen in FIG. 18, a top surface of set screw 60 is flush with weakened region 410 of loading unit 400. Upon fully securing connecting rod 10 in slot 353, the clinician may detach loading unit 400 from head portion 352 of bone screw 350 by, e.g., cutting through weakened region 410 using a surgical knife (not shown), as shown in FIGS. 19 and 20. Alternatively, repeated bending of walls 402, 404 towards and away from central longitudinal axis "Z-Z" of screw 350 causes separation of walls 402, 404 from loading unit 400 along weakened region 410.

Shank 354 includes threads 355 for engagement through vertebral bodies. Bone screw 50 may be made of a biocompatible material such as Titanium (Ti-CP) and its alloys (e.g., Ti-6A1-4V), Cobalt-Chrome Alloy (CoCr) or Stainless Steel (SS). In particular, head portion 52 and shank 54 may be monolithically formed. The method of using spinal stabilization system 300 is substantially similar to the method of using spinal stabilization system 100, described hereinabove, and thus will not be discussed herein.

Although the illustrative embodiments of the present disclosure have been described herein with reference to the accompanying drawings, the above description, disclosure, and figures should not be construed as limiting, but merely as exemplifications of particular embodiments. One skilled in the art will recognize that the present disclosure is not limited to use in spine surgery, and that the instrument and methods can be adapted for use with any suitable surgical device. It is to be understood, therefore, that the disclosure is not limited to those precise embodiments, and that various other changes and modifications may be effected therein by one skilled in the art without departing from the scope or spirit of the disclosure.

What is claimed is:

1. A spinal stabilization system comprising:
   a connecting rod including an elongate rounded section having a circular cross-section, an elongate head portion having a non-circular cross-section, and a neck portion connecting the elongate rounded section with the elongate head portion, the connecting rod being monolithically formed, wherein a centroid of the neck portion is closer to a centroid of the elongate head portion than a centroid of the elongate rounded section; and
   a bone screw defining a longitudinal axis, the bone screw including a head portion defining a slot, and a shank extending from the head portion, the head portion defining the slot having a U-shape orthogonal to the longitudinal axis of the bone screw to receive the connecting rod, wherein a portion of the slot is complementary to the elongate rounded section of the connecting rod.

2. The spinal stabilization system according to claim 1, wherein the head portion of the bone screw includes a trailing wall and a leading wall, the trailing wall including a lip extending radially inward, the lip defining an aperture.

3. The spinal stabilization system according to claim 2, wherein at least one of the leading wall or the trailing wall includes a surface configured to engage a portion of the elongate head portion of the connecting rod.

4. The spinal stabilization system according to claim 3, wherein the surface of the at least one of the leading wall or the trailing wall is planar to inhibit rotation of the connecting rod when the connecting rod is disposed in the slot of the head portion of the bone screw.

5. The spinal stabilization system according to claim 2, wherein the bone screw further includes a set screw and the lip of the trailing wall includes threads configured to engage threads on the set screw.

6. The spinal stabilization system according to claim 1, wherein the slot of the head portion of the bone screw is dimensioned to inhibit rotation of the connecting rod when the connecting rod is disposed in the slot.

7. The spinal stabilization system according to claim 1, wherein the bone screw is formed of a biocompatible material.

8. A spinal stabilization system comprising:
   a connecting rod including an elongate rounded section having a circular cross-section, an elongate head portion having an elongated, non-circular cross-section, and a neck portion connecting the elongate rounded section with the elongate head portion by extending from the elongate rounded section to the elongate head portion along a neck axis, the connecting rod being monolithically formed,
   wherein a centroid of the neck portion is closer to a centroid of the elongate head portion than a centroid of the elongate rounded section; and
   a bone screw including a head portion defining a slot, a shank extending from the head portion, and a set screw configured to secure the connecting rod in the slot, the head portion including a leading wall, a trailing wall, and a transverse wall connecting the leading and trailing walls, the slot defined between the leading and trailing walls, the trailing wall defining an aperture dimensioned to receive the set screw, the aperture in communication with the slot, the transverse wall includes an arcuate portion configured to receive the elongate rounded section of the connecting rod.

9. The spinal stabilization system according to claim 8, wherein the trailing wall includes a lip extending radially inward, the lip defining the aperture.

10. The spinal stabilization system according to claim 9, wherein the lip includes threads configured to engage threads on the set screw.

11. The spinal stabilization system according to claim 8, wherein the slot is substantially U-shaped.

12. The spinal stabilization system according to claim 11, wherein the slot is substantially orthogonal to a longitudinal axis defined by the bone screw.

13. The spinal stabilization system according to claim 8, wherein the elongated cross-section of the elongate head portion has a length dimension and a width dimension, the width dimension being smaller than the length dimension, and the length dimension extending transverse to the neck axis.

14. A method of surgery comprising:
   inserting a first bone screw into a vertebral body;
   bending a connecting rod including an elongate rounded section having a circular cross-section, an elongate head portion having a non-circular cross-section, and a neck portion connecting the elongate rounded section with the elongate head portion to conform to a desired configuration, the connecting rod being monolithically formed,
   wherein a centroid of the neck portion is closer to a centroid of the elongate head portion than a centroid of the elongate rounded section;
   positioning the connecting rod in a slot defined in a head portion of the first bone screw, the slot including an opening orthogonal to a longitudinal axis of the first bone screw, the slot including an arcuate portion complementary to the elongate rounded section of the connecting rod; and
   securing the elongate head portion of the connecting rod with the head portion of the first bone screw.

15. The method according to claim 14, wherein positioning the connecting rod includes positioning the connecting rod in the slot through the opening interposed between trailing and leading walls of the head portion of the first bone screw.

16. The method according to claim 15, wherein securing the elongate head portion of the connecting rod includes threading a set screw through an aperture defined in the trailing wall of the head portion of the first screw such that the set screw engages the elongate head portion of the connecting rod disposed in the slot.

17. The method according to claim 14, further comprising adjusting a curve of the spine prior to securing the connecting rod with the first bone screw.

\* \* \* \* \*